(12) United States Patent
Stango

(10) Patent No.: US 10,973,533 B2
(45) Date of Patent: Apr. 13, 2021

(54) BONE MILL HAVING GRINDING SURFACES PROVIDED WITH ANTI-BINDING DEAD-STOPS

(71) Applicant: HU-FRIEDY MFG. CO., LLC, Chicago, IL (US)

(72) Inventor: James Christopher Stango, Chicago, IL (US)

(73) Assignee: HU-FRIEDY MFG. CO., LLC, Chicago, IL (US)

(*) Notice: Subject to any disclaimer, the term of this patent is extended or adjusted under 35 U.S.C. 154(b) by 148 days.

(21) Appl. No.: 16/372,042

(22) Filed: Apr. 1, 2019

(65) Prior Publication Data

US 2019/0328404 A1 Oct. 31, 2019

Related U.S. Application Data

(60) Provisional application No. 62/662,508, filed on Apr. 25, 2018.

(51) Int. Cl.
| | |
|---|---|
| A61B 17/16 | (2006.01) |
| A61F 2/46 | (2006.01) |
| A61C 8/00 | (2006.01) |
| A61F 2/28 | (2006.01) |

(52) U.S. Cl.
CPC ...... *A61B 17/1635* (2013.01); *A61B 17/1673* (2013.01); *A61C 8/0089* (2013.01); *A61F 2/28* (2013.01); *A61F 2/4644* (2013.01); *A61B 17/1615* (2013.01); *A61B 2017/1602* (2013.01); *A61F 2002/2835* (2013.01); *A61F 2002/4645* (2013.01)

(58) Field of Classification Search
CPC ............ A61B 17/16; A61B 2017/1602; A61B 17/1613; A61B 17/1615; A61B 17/1635; A61B 17/1673; A61F 2/4644; A61F 2002/4645; B02C 7/02; B02C 7/04; B02C 7/08; B02C 19/0056; B02C 19/20; A22C 17/06; A24B 7/06; A47J 42/20
See application file for complete search history.

(56) References Cited

U.S. PATENT DOCUMENTS

| | | | |
|---|---|---|---|
| 354,863 A | 12/1886 | Hughes | |
| 3,755,902 A | 9/1973 | Northcutt | |
| 6,287,312 B1 * | 9/2001 | Clokie | A61F 2/4644 606/85 |
| 7,431,230 B2 * | 10/2008 | McPherson | A61F 2/4644 241/169 |
| D806,875 S * | 1/2018 | de Quincey | D24/152 |

FOREIGN PATENT DOCUMENTS

| | | | | |
|---|---|---|---|---|
| DE | 2519848 A1 * | 2/1976 | | B02C 7/04 |
| DE | 19801218 A1 | 7/1999 | | |
| DE | 102007011992 B3 | 4/2008 | | |
| DE | 2519848 | * 11/2020 | | |

OTHER PUBLICATIONS

European Patent Application No. 19167908.3, Extended European Search Report, dated Aug. 21, 2019.

* cited by examiner

*Primary Examiner* — Larry E Waggle, Jr.
(74) *Attorney, Agent, or Firm* — Marshall, Gerstein & Borun LLP

(57) ABSTRACT

A bone milling device for grinding bone during a bone grafting procedure including a pair of opposing dead stops, one or more provided on a rotating plate of a rotatable mill and one or more provided on a stationary plate to prevent adhesion of respective arrays of grinding teeth.

28 Claims, 5 Drawing Sheets

US 10,973,533 B2

BONE MILL HAVING GRINDING SURFACES PROVIDED WITH ANTI-BINDING DEAD-STOPS

CROSS-REFERENCE TO RELATED APPLICATION

This non-provisional application claims the benefit of the filing date of U.S. Provisional Application No. 62/662,508, filed Apr. 25, 2018, the entirety of which is hereby incorporated by reference.

BACKGROUND

Field of the Disclosure

The present disclosure relates generally to the field of dental instruments used during bone grafting in dental implant procedures and, more specifically, to an improvement to the grinding surfaces of jaws of a bone mill.

BRIEF SUMMARY OF THE DISCLOSURE

It is known to reinforce an area surrounding a dental implant site by applying a bone graft to a cavity created in a jaw bone. For instance, a known technique for grafting bone during a dental implant procedure, called an autogenous bone graft, involves creating a cavity in a jaw bone at the site of the future dental implant, milling a patient's bone that was extracted during a previous procedure, and placing the milled bone in the cavity. The autogenous bone graft is considered advantageous over an allogenic bone graft (i.e., a bone graft using dead bone harvested from a cadaver) and a xenogenic bone graft (i.e., a bone graft using non-living bone from another species, such as bovine) because the autogenous bone graft contains living cellular elements that enhance and encourage bone growth. The allogenic and xenogenic bone grafts do not contain living cellular elements and, thus, simply act as a framework for the patient's jaw bone to grow over. However, autogenous bone grafts unfavorably require a first procedure to harvest the patient's bone prior to the dental implant procedure.

It is also challenging to manually mill the patient's bone after harvesting bone from, for example, a hip bone. For instance, a known technique for milling bone involves placing pieces of the harvested bone between two grinding surfaces and rotating one of the grinding surfaces while simultaneously advancing one grinding surface toward the other. As the two grinding surfaces converge, milled bone accumulates in interstices between grinding teeth defining each of the grinding surfaces. The accumulation increases as one grinding surface nears the other, causing the milled bone to become compacted, while the grinding teeth from each of the grinding surfaces forcefully compact the accumulation of milled bone further into the interstices. This combination of milled bone buildup in the interstices and the forces exerted by the grinding surfaces while milling the pieces of bone causes the grinding surfaces to bind, or adhere to each other, making it difficult to separate the grinding surfaces to retrieve the milled bone. The device of the present disclosure achieves reliable milling of harvested bone and prevents the grinding surfaces from adhering (i.e., binding) to one another.

DETAILED DESCRIPTION OF THE PREFERRED EMBODIMENTS

Embodiments disclosed herein generally relate to devices for milling bone and, more specifically, to devices for milling bone for preparing grafts to use during dental implant procedures.

Figure 1:
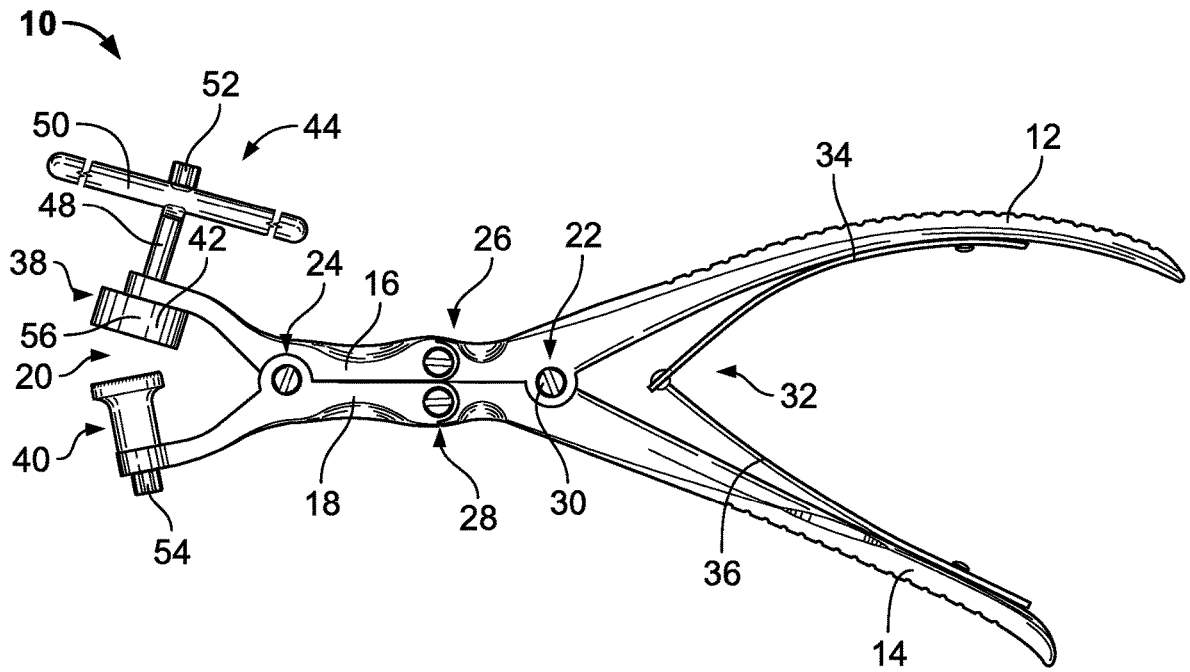
FIG. 1 is a plan view of a bone mill of a first embodiment of the present disclosure, in an open position.
Figure 2:
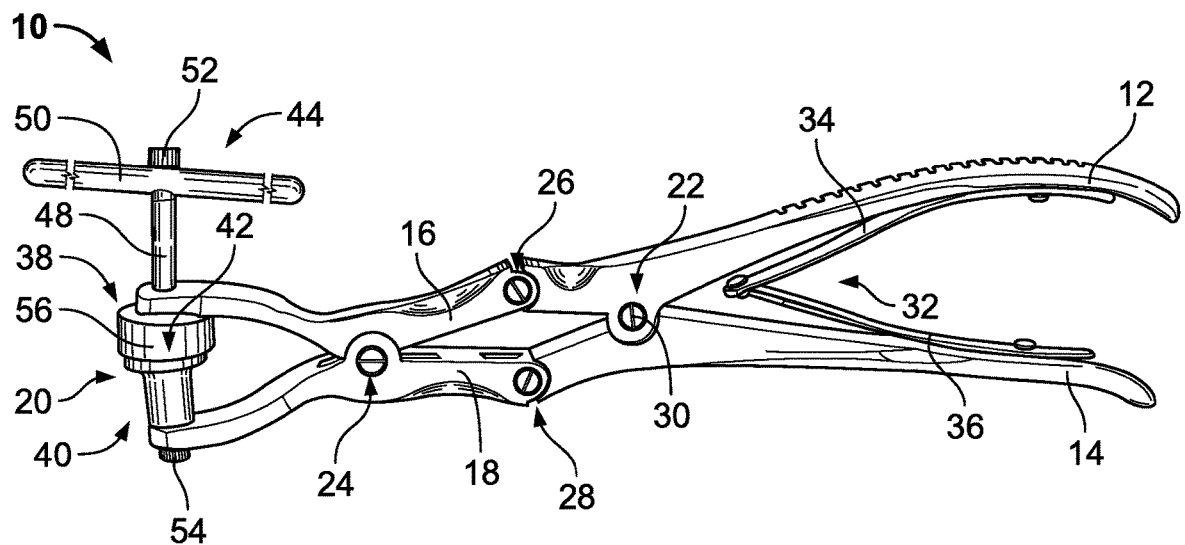
FIG. 2 is a perspective view of the bone mill of FIG. 1 in a closed position.

The bone mill device 10 of the present disclosure includes a first grip 12, a second grip 14, a first arm 16, a second arm 18, and a bone milling assembly 20. As best illustrated in FIGS. 1 and 2, a first hinge 22 connects the first grip 12 to the second grip 14 and a second hinge 24 connects the first arm 16 to the second arm 18. A third hinge 26 connects the first arm 16 to the first grip 12 and a fourth hinge 28 connects the second arm 18 to the second grip 14. In a first embodiment, the first, second, third, and fourth hinges 22, 24, 26, 28 are secured using a pin 30. Additionally, the third and fourth hinges 26, 28 may be disposed between the first and second hinges 22, 24.

The first grip 12 may have an arced profile while the second grip 14 may have a linear profile, so the device 10 rests ergonomically in a user's hand. Additionally, the first and second grips 12, 14 may have notches along an outer surface of the first and second grips 12, 14 to improve grip and minimize slipping or sliding of the device 10 while in a user's hand during use. In the first embodiment, a parabolic leaf spring 32 is disposed between and fixedly attached to the first and second grips 12, 14. The parabolic leaf spring 32 acts to keep the jaws of the bone milling assembly 20 separated from one another while the device 10 is not in use. The parabolic leaf spring 32 may include a distal end of a first spring 34 connected to a distal end of a second spring 36 via, for example, a rivet. A proximal end of the first spring 34 is fixedly attached to an inner surface of the first grip 12 and a proximal end of the second spring 36 is fixedly attached to an inner surface of the second grip 14. In another embodiment, the parabolic leaf spring 32 may take the form of a traditional coil spring disposed between the first and second grips 12, 14.

The bone milling assembly 20 includes a rotatable mill 38, a stationary mill 40, and a hollow cylinder 42. In a first embodiment, the rotatable mill 38 and the hollow cylinder 42 are disposed at a distal end of the first arm 16 and the stationary mill 40 is disposed at a distal end of the second arm 18. In a second embodiment, the rotatable mill 38 and the hollow cylinder 42 are disposed at the distal end of the second arm 18 and the stationary mill 40 is disposed at the distal end of the first arm 16. In either embodiment, the rotatable mill 38 includes a handle 44 that extends perpendicularly from a rotating plate 46. The handle 44 includes a shaft 48 fixedly secured to the rotating plate 46 and a transverse member 50 removably secured to a distal end of the shaft 48. In the first embodiment, the transverse member 50 takes the form of a single, elongate member that slides into a semi-circular cavity near the distal end of the shaft 48. To secure the transverse member 50 to the shaft 48, the distal end of the shaft 48 is threaded to receive a threaded cap 52. As the threaded cap 52 is attached to the distal end of the shaft 48, the transverse member 50 is secured to the shaft 48 by the force applied by the threaded cap 52 once secured.

Figure 3:
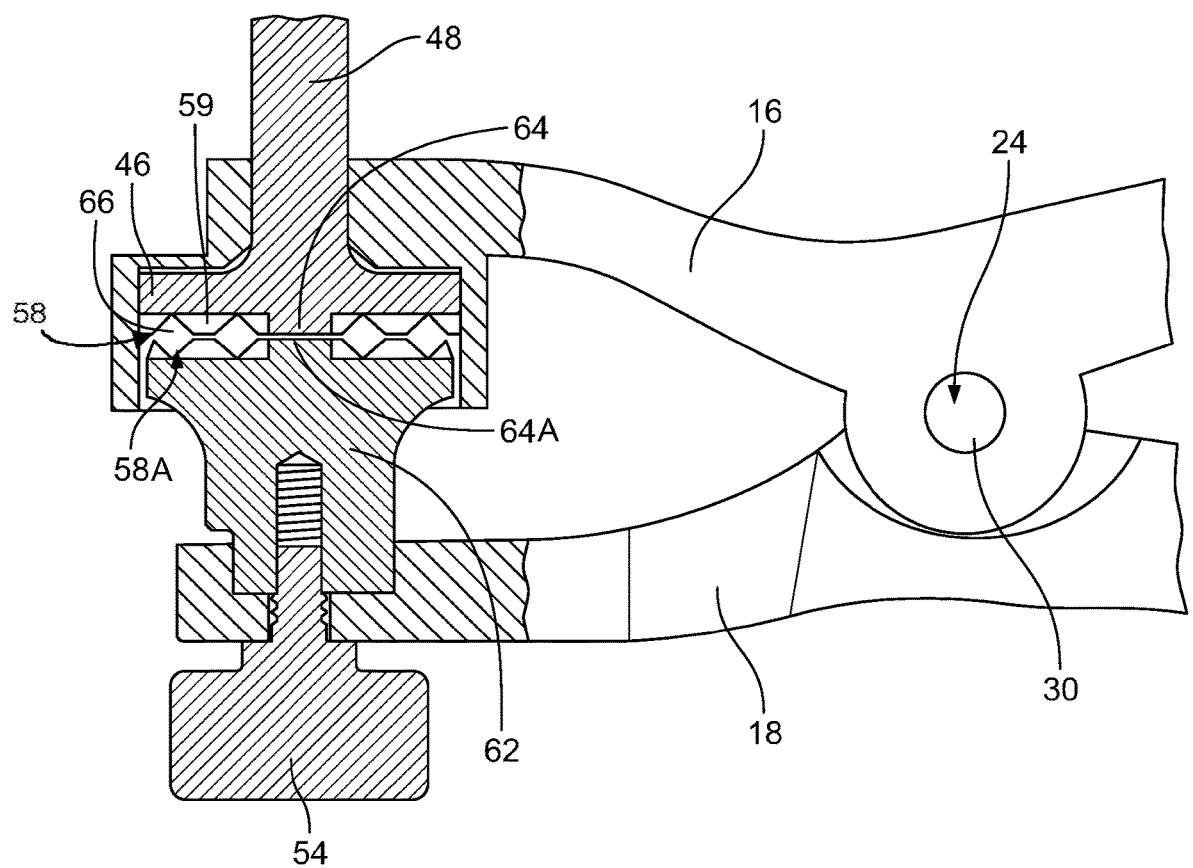
FIG. 3 is a cross-sectional view of a bone grinding assembly of the bone mill of FIG. 1.

As is best illustrated in FIG. 3, removably securing the stationary mill 40 to the distal end of the second arm 18 involves using, for example, a screw 54. The screw 54 threadably engages a threaded cavity disposed within the stationary milling tool 40. Additionally, the hollow cylinder 42 is fixedly attached to the distal end of the first arm 16. In the first embodiment, the hollow cylinder 42 extends perpendicularly from an interior surface of the first arm 16 (i.e., toward the second arm 18). The hollow cylinder 42 slidably receives the rotatable mill 38 through an aperture in a bottom surface of the hollow cylinder 42 that extends through the first arm 16. Further, the hollow cylinder 42 may be sized such that a diameter of an inner wall of the cylinder 42 is equal to or slightly greater than a diameter of the rotating plate 46. Sizing the cylinder 42 in such a manner limits large pieces of bone from wedging between the rotating plate 48 and the bottom surface of the hollow cylinder 42.

As is best illustrated in FIGS. 4, 5, 6, 7, and 8, the rotating plate 46 is disposed at a distal end of the rotatable mill 38 and a stationary plate 62 is disposed at a distal end of the stationary mill 40. An array of grinding teeth 58 ("the array 58") is fixed to the rotating plate 46 and projects outwardly (i.e., toward the stationary plate 62). Additionally, a substantially similar array 58A is fixed to the stationary plate 62 and projects outwardly (i.e., toward the rotating plate 46). A grinding tooth 59, 59A part of each array 58, 58A may take, for example, a shape and a height most suitable to achieve the desired grain size of the milled bone. In particular, each grinding tooth 59, 59A in the arrays 58, 58A may take the shape of a truncated pyramid, with each grinding tooth 59, 59A being of equal height.

Each array 58, 58A and the arrangement of grinding teeth 59, 59A in the respective array are best understood with reference to FIGS. 4, 5, 7 and 8. In particular, a base of one grinding tooth 59 in the array 58 abuts an edge of the base of four other grinding teeth 59. The density of the grinding teeth 59 in the array 58 depends on the desired bone grain size. For example, if a fine grain size is desired, there will be a greater density of grinding teeth 59 in the array 58. Thus, in such an embodiment, the grinding teeth 59 are a smaller shape and relatively tightly packed together in the array 58. Conversely, if a coarse grain size is desired, there will be a low density of grinding teeth 59 in the array 58. Thus, in such an embodiment, the grinding teeth 59 are larger and relatively loosely packed together in the array 58. Additionally, the example embodiment illustrated in FIGS. 4, 5, 7 and 8 depicts a symmetrical arrangement of the grinding teeth 59 in the array 58, but the arrangement of grinding teeth 59 in the array 58 need not be symmetrical.

Figure 4:
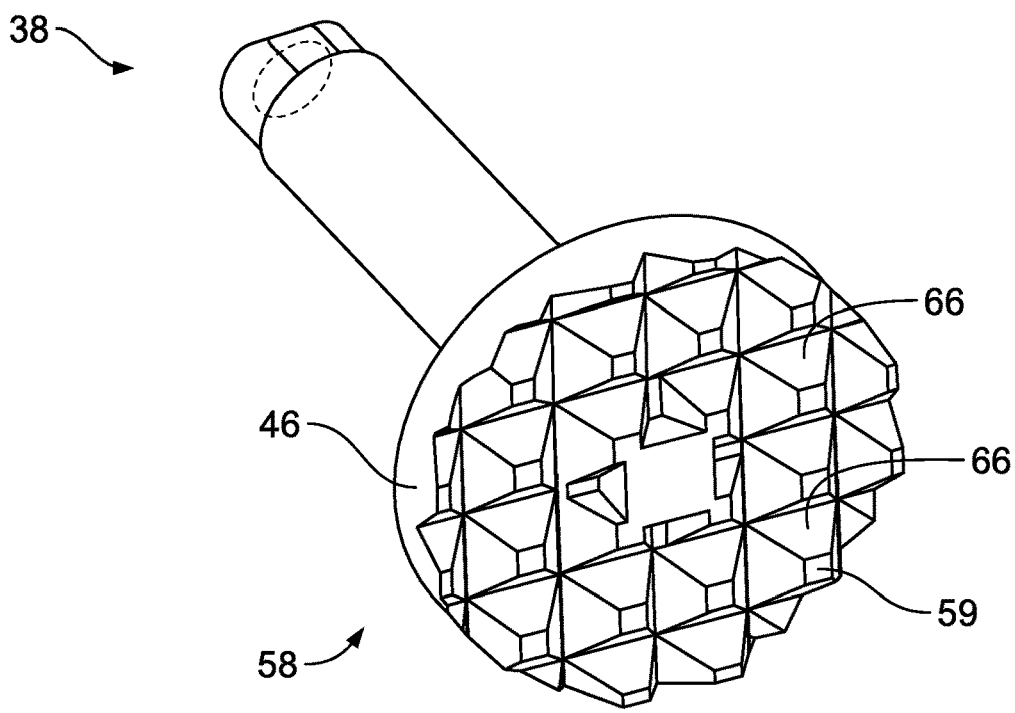
FIG. 4 is a perspective view of a first embodiment of a rotatable mill of the bone mill of FIG. 1, with the remainder of the bone mill assembly removed.
Figure 5:
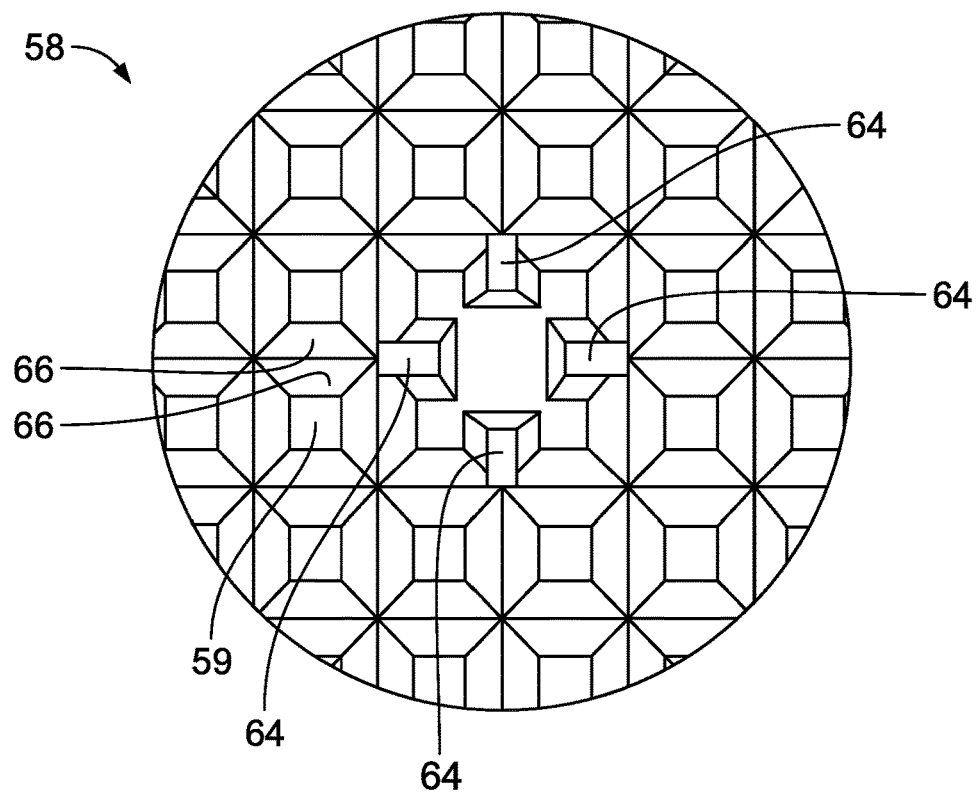
FIG. 5 is a plan view of a first embodiment of an array of grinding teeth of the first embodiment of the bone mill of the present disclosure.

Each of the rotating plate 46 and the stationary plate 62 is provided with a dead-stop 64, 64A to prevent the grinding teeth 59, 59A in the arrays 58, 58A from entering the interstices 66 between the grinding teeth 59A, 59 in the opposing array 58A, 58. In the first embodiment, the dead-stop 64 is disposed centrally on the rotating plate 46 and the stationary plate 62 (i.e., the rotating plate's dead-stop 64 and the stationary plate's dead-stop 64A are concentric). The dead-stops 64, 64A may, for example, take a shape and a placement that best suits the arrangement of the grinding teeth 59, 59A in the arrays 58, 58A. In particular, as illustrated in FIG. 4, four dead stops are disposed around a central axis of each plate 46, 62 at an angle of ninety (90) degrees relative to each other. Additionally, the dead-stop 64 may take the form of a rectangular elongation projecting outwardly from the rotating plate 46 or the stationary plate 62 (i.e., toward the stationary plate 62 or toward the rotating plate 46, respectively).

Figure 7:
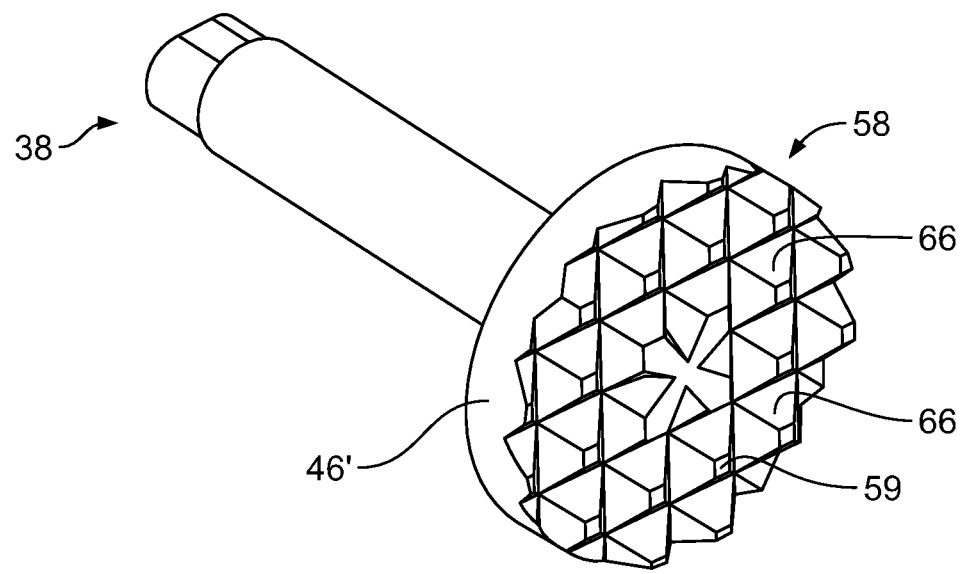
FIG. 7 is a perspective view of a second embodiment of the rotatable mill of the bone mill of FIG. 1, with the remainder of the bone mill assembly removed for the sake of clarity.
Figure 8:
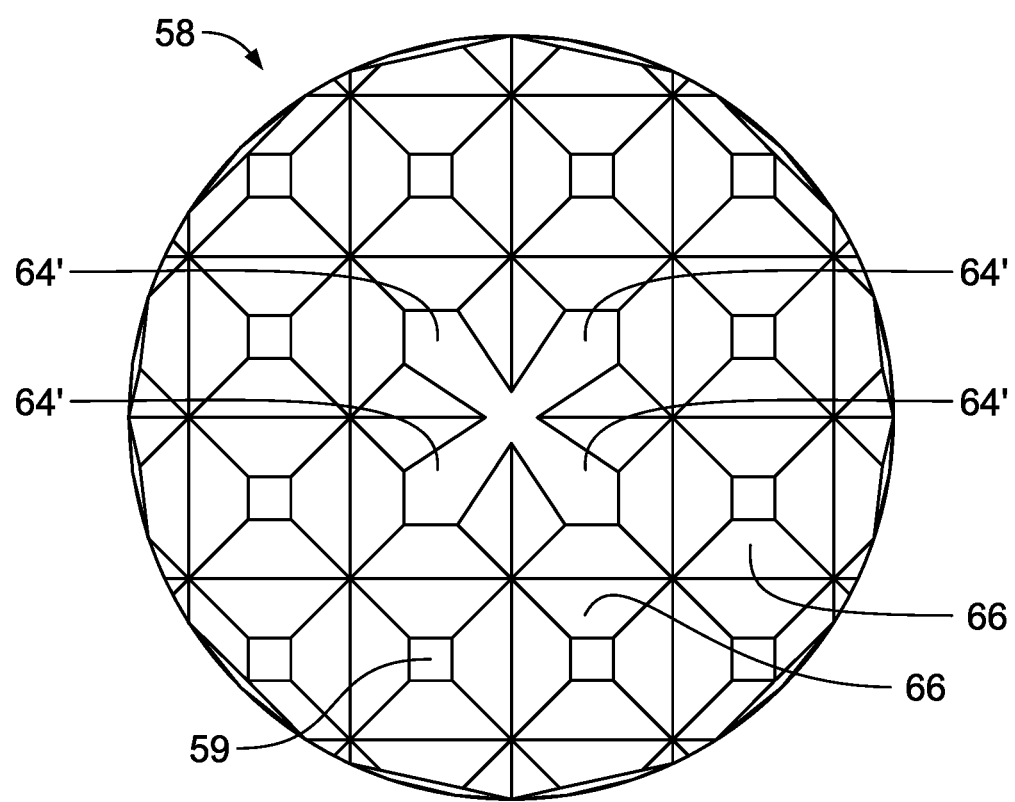
FIG. 8 is a plan view of an array of grinding teeth of the second embodiment of the bone mill of the present disclosure.

FIGS. 7 and 8 illustrate a second embodiment of a rotating plate 46' and the stationary plate. The rotating plate 46' and the stationary plats 62' illustrated in FIGS. 7 and 8 and the stationary plate (not shown) are similar to the rotating plate 46 and the stationary plate 62 illustrated in FIGS. 4 and 5, with common components illustrated using common reference numerals, but differ in that rotating plate 46' and stationary plate 64' include a dead-stop 64' that, while otherwise similar, has a layout that is different from the dead-stop 64. More particularly, like the dead-stop 64, the dead-stop 64' prevents the grinding teeth 59, 59A in the arrays 58, 58A from entering the interstices 66 between the grinding teeth 59A, 59 in the opposing array 58A, 58. However, unlike the dead-stop 64, the dead-stop 64' is disposed around the central axis of each plate 46', such that the joined region of the multiple dead stops generally forms the shape of an "X."

Figure 6:
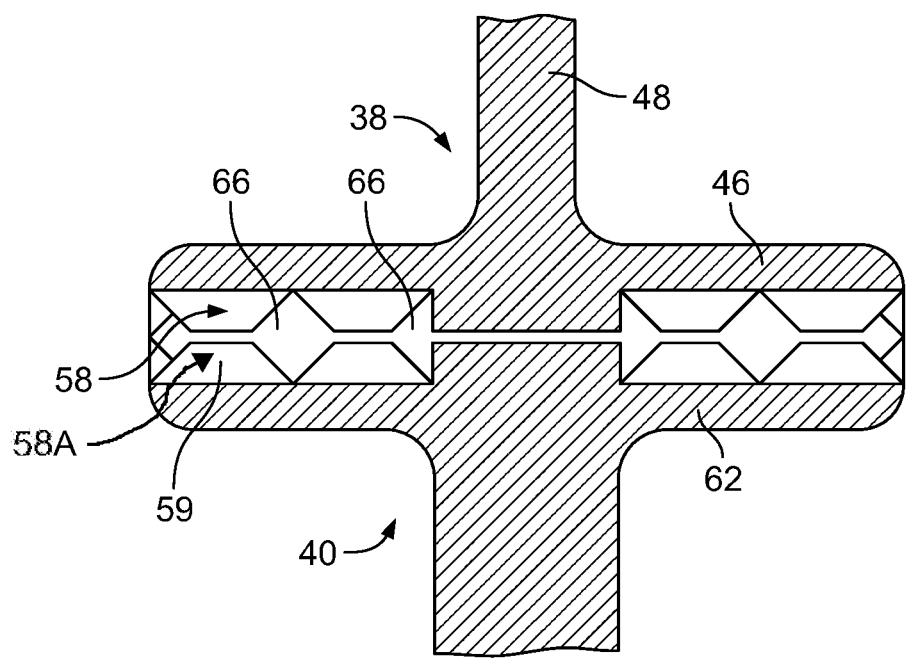
FIG. 6 is a cross-sectional view of the bone grinding assembly of FIG. 3 with a portion of the bone mill removed.

Further, the height of the dead-stops 64, 64A depends on the height of the grinding teeth 59, 59A in the array 58. For example, in a first embodiment, the height of the dead-stop 64 is equal to the height of the grinding teeth 59 in the array 58 (i.e., flush with the array 58), ensuring the rotating plate's dead-stop 64 makes contact with the stationary plate's dead-stop 64A prior to the grinding teeth 59 of either the rotating plate 46 or the stationary plate 62 falling into the interstices 66 or making contact with another grinding tooth 59, 59A. As illustrated in FIG. 6, the dead-stop 64 prohibits the rotating plate's grinding teeth 59 from making contact with the stationary plate's grinding teeth 59A, thereby preventing the rotatable mill 38 from adhering to the stationary mill 40.

To describe using the device 10 in accordance with the present disclosure, reference is made to FIGS. 1 and 2. In a first embodiment, the pieces of bone are placed on either the rotating plate 46 or the stationary plate 62. Squeezing the first and second grips together (i.e., pushing down the first grip and simultaneously pulling up on the second grip) advances the rotatable mill and stationary mill toward each other (i.e., the rotatable mill 38 and stationary mill 40 converge concentrically). As illustrated in FIG. 2, the first grip's 12 distal end translates in an upward motion (i.e., away from the second grip 14) and the second grip's 14 distal end translates in a downward motion (i.e., away from the first grip 12) as the first and second grips 12, 14 are squeezed together. The third and fourth hinges 26, 28 convert the motion of the distal ends of the first and second grips 12, 14 into a downward motion of the first arm's 16 distal end (i.e., toward the second arm 18) and an upward motion of the second arm's 18 distal end (i.e., toward the first arm 16).

The movement of the first and second arms 16, 18 converges the rotatable mill 38 and the stationary mill 40. The arrangement of the hinges 22, 24, 26, 28 shown in FIGS. 1 and 2 open the rotatable mill 38 and the stationary mill 40 at an angle, rather than vertically translating the mills 38, 40. Opening the mills 38, 40 at an angle facilitates removal of the milled pieces of bone. Additionally, the motion of the first and second arms 16, 18 ensures that the rotatable mill's dead-stops 64 and the stationary mill's dead-stop 64A coaxially align as the mills converge. In other words, as the rotatable and stationary mills 38, 40 simultaneously move toward one another, the mills 38, 40 level out such that the rotating plate 46 is parallel to the stationary plate 62 before the pieces of bone are milled.

Rotating the handle 44 while squeezing the first and second grips 12, 14 together exerts a continuous rotational pressure on the pieces of bone, milling the pieces of bone into smaller pieces. Pressure is continuously applied to the pieces of bone while turning the handle 44 until the rotatable mill's 38 dead-stop 64 makes contact with the stationary mill's 40 dead-stop 64A. Since the height of the dead-stops 64, 64A on the rotatable mill 38 and the stationary mill 40 are equal to the height of the grinding teeth 59 in the arrays 58 of the respective tools, the dead-stop 64 prevents the grinding teeth 59 fixed to the rotating plate 46 from falling into the interstices 66 between the grinding teeth 59A fixed to the stationary plate 62A, and vice-versa. This advantageously creates a gap between the array 58 fixed to the rotating plate 46 and the array 58 fixed to the stationary plate 62 ensuring the grinding teeth 59, 59A of the respective plates 46, 62 do not adhere to each other.

While the present device has been described with respect to various specific embodiments, it will be understood that variations may be made that are still within the scope of the present disclosure. The appended claims are not intended to be limited to the details of the specific embodiments disclosed herein.

What is claimed is:

1. A bone milling device for grinding bone during a bone grafting procedure, the device comprising:
   a rotatable mill disposed within a cavity of a cylinder having a rotating plate and a handle extending perpendicularly from a side opposite the rotating plate, the rotating plate having an array of grinding teeth fixedly attached thereto and projecting in a direction opposite to the handle, and a dead-stop extending perpendicularly from the rotating plate in the same direction as the array of grinding teeth of the rotatable mill; and
   a stationary mill disposed opposite the rotatable mill at a proximal end of a second arm having a stationary plate, the stationary plate having an array of grinding teeth fixedly attached thereto and projecting toward the array of teeth of the rotatable mill and a dead-stop extending perpendicularly from the stationary plate in the same direction as the array of grinding teeth of the stationary mill, the dead-stop of each of the rotatable plate and the stationary plate extending outwardly from a central axis of the respective rotating plate along a plane of contact with the opposing dead-stop.

2. The device of claim 1 wherein the dead-stop of the rotatable mill and the dead-stop of the stationary mill are concentrically aligned.

3. The device of claim 1 wherein the rotating mill is in the shape of a circle.

4. The device of claim 1 wherein the stationary mill is in the shape of a circle.

5. The device of claim 1 wherein the array of grinding teeth of the rotatable mill and the dead-stop of the rotatable mill are removably coupled to the rotating plate.

6. The device of claim 1 wherein the array of grinding teeth of the rotatable mill and the dead-stop of the rotatable mill are integrally formed with the rotating plate.

7. The device of claim 1 wherein the dead-stop of the rotatable mill is arranged on the rotatable mill such that the dead-stop of the rotatable mill forms a circle that is centrally located on the rotatable mill.

8. The device of claim 1 wherein the dead-stop of the rotatable mill is arranged on the rotatable mill such that the dead-stop of the rotatable mill forms an X shape that is centrally located on the rotatable mill.

9. The device of claim 1 wherein the array of grinding teeth of the stationary mill and the dead-stop of the stationary mill are removably coupled to the stationary plate.

10. The device of claim 1 wherein the array of grinding teeth of the stationary mill and the dead-stop of the stationary mill are integrally formed with the stationary plate.

11. The device of claim 1 wherein the dead-stop of the stationary mill is arranged on the stationary mill such that the dead-stop of the stationary mill forms a circle that is centrally located on the rotatable mill.

12. The device of claim 1 wherein the dead-stop of the stationary mill is arranged on the stationary mill such that the dead-stop of the stationary mill forms an X shape that is centrally located on the rotatable mill.

13. A bone milling device for use during dental implant procedures, the device comprising:
   a first grip connected to a second grip via a first hinge, the first hinge disposed toward a distal end of the first grip and a distal end of the second grip, a first arm connected to a second arm via a second hinge, the second hinge disposed toward a distal end of the first arm and a distal end of the second arm, the first grip connected to the first arm via a third hinge, the third hinge disposed toward a distal end of the first grip and a proximal end of the first arm, and the second grip connected to the second arm via a fourth hinge, the fourth hinge disposed toward a distal end of the second grip and a proximal end of the second arm;
   a bone milling assembly, comprising:
   a hollow cylinder disposed at the distal end of the first arm having a wall extending perpendicularly around a circumference of the hollow cylinder creating a cavity to receive pieces of bone; and
   a rotatable mill disposed within the cavity of the hollow cylinder having a rotating plate and a handle extending perpendicularly from a side opposite the rotating plate, the rotating plate having an array of grinding teeth fixedly attached thereto and projecting outwardly and a dead-stop extending perpendicularly from the rotating plate; and
   a stationary mill disposed opposite the rotatable mill at the distal end of the second arm having a stationary plate, the stationary plate having an array of grinding teeth fixedly attached thereto and projecting outwardly and a dead-stop extending perpendicularly from the stationary plate, the dead-stop of each of the rotatable plate and the stationary plate extending outwardly from a central axis of the respective rotating plate along a plane of contact with the opposing dead-stop;
   wherein, the dead-stop of the rotating plate contacts the dead-stop of the stationary plate prior to the array of grinding teeth of the rotating plate contacting the array of grinding teeth of the stationary plate creating a gap that limits adhesion between the array of grinding teeth of the rotatable plate and the array of grinding teeth of the stationary plate.

14. The device of claim 13 wherein the rotating plate is in the shape of a circle.

15. The device of claim 13 wherein the stationary plate is in the shape of a circle.

16. The device of claim 13 wherein the handle further comprises a shaft and a transverse member, the shaft fixedly attached to the side opposite the rotating plate at a proximal end of the shaft and the transverse member attached perpendicularly to a distal end of the shaft.

17. The device of claim 16 wherein the transverse member is removably attached to the shaft.

18. The device of claim 13 wherein the stationary mill is fixedly attached to the distal end of the second arm via a screw or weld.

19. The device of claim 13 wherein the dead-stop of the rotatable mill and the dead-stop of the stationary mill are concentrically aligned.

20. The device of claim 13 wherein the rotating plate and the handle of the rotatable mill are integrally formed.

21. The device of claim 13 wherein the array of grinding teeth and the dead-stop of the rotatable mill are removably coupled to the rotating plate.

22. The device of claim 13 wherein the array of grinding teeth of the rotatable mill and the dead-stop of the rotatable mill are integrally formed with the rotating plate.

23. The device of claim 13 wherein the dead-stop of the rotatable mill is arranged on the rotatable mill such that the dead-stop of the rotatable mill forms a circle that is centrally located on the rotatable mill.

24. The device of claim 13 wherein the dead-stop of the rotatable mill is arranged on the rotatable mill such that the dead-stop of the rotatable mill forms an X shape that is centrally located on the rotatable mill.

25. The device of claim 13 wherein the array of grinding teeth of the stationary mill and the dead-stop of the stationary mill are removably coupled to the stationary plate.

26. The device of claim 13 wherein the array of grinding teeth of the stationary mill and the dead-stop of the stationary mill are integrally formed with the stationary plate.

27. The device of claim 13 wherein the dead-stop of the stationary mill is arranged on the stationary mill such that the dead-stop of the stationary mill forms a circle that is centrally located on the stationary mill.

28. The device of claim 13 wherein the dead-stop of the stationary mill is arranged on the stationary mill such that the dead-stop of the stationary mill forms an X shape that is centrally located on the stationary mill.

* * * * *